United States Patent [19]
Hayashizaki

[11] Patent Number: 5,856,100
[45] Date of Patent: Jan. 5, 1999

[54] METHOD FOR PURIFICATION AND TRANSFER TO SEPARATION/DETECTION SYSTEMS OF DNA SEQUENCING SAMPLES AND PLATES USED THEREFOR

[75] Inventor: Yoshihide Hayashizaki, Tsukuba, Japan

[73] Assignee: The Institute of Physical and Chemical Research, Japan

[21] Appl. No.: 764,107

[22] Filed: Dec. 6, 1996

[30] Foreign Application Priority Data

Dec. 8, 1995 [JP] Japan ................................. 7-320732

[51] Int. Cl.⁶ ............................. C12Q 1/68; C07H 21/00
[52] U.S. Cl. ................................. 435/6; 536/254
[58] Field of Search ................... 435/6, 5, 91.2, 435/284, 809, 305.3, 305.2, 288.5, 288.6; 204/455, 451, 601; 536/25.4

[56] References Cited

U.S. PATENT DOCUMENTS 5,415,758  5/1995  Comeau ........................ 204/299 R
5,560,811  10/1996  Briggs et al. ........................ 204/451

FOREIGN PATENT DOCUMENTS 0131934  1/1985  European Pat. Off. .
WO88/06723  9/1988  WIPO .
WO94/29712  12/1994  WIPO .

OTHER PUBLICATIONS

Cole PArmer Catalog, 1993.
Xiaohua C. Huang et al., "DNA Sequencing Using Capillary Array Electrophoresis", *Analytical Chemistry* (1992) 64:2149–2154, No. 18.

*Primary Examiner*—W. Gary Jones
*Assistant Examiner*—Debra Shoemaker
*Attorney, Agent, or Firm*—Burns, Doane, Swecker & Mathis, L.L.P.

[57] ABSTRACT

Disclosed are: a part for assembling reaction vessels comprising a base plate with holes passing through said plate in the direction of thickness; a method for preparation of reaction vessels containing a reaction solution characterized in that the part is immersed in a reaction solution to introduce the reaction solution into the holes and then one of apertures of each hole is sealed with a membrane to complete said reaction vessels; and a plate comprises a base plate with holes passing through the plate in the direction of thickness and a membrane for sealing one of the apertures of each hole. The plate is used for purification of DNA sequencing samples using a pressure difference or an electrical potential, and transferring DNA sequencing samples to a separation/detection system. By the means or the method of the invention, reaction solutions can be easily introduced into a large number of wells in a short time, unreacted labeling substances and the like can be easily removed in a short time from a plurality of DNA sequencing samples, and a large number of DNA sequencing samples can be easily purified and/or transferred to electrophoresis capillaries in a short time.

14 Claims, 8 Drawing Sheets

METHOD FOR PURIFICATION AND TRANSFER TO SEPARATION/DETECTION SYSTEMS OF DNA SEQUENCING SAMPLES AND PLATES USED THEREFOR

BACKGROUND OF THE INVENTION

The present invention relates to a plate used for transferring DNA sequencing samples to a separation/detection system. The plate of the present invention is capable of transferring at one and the same time a plurality of reaction products produced in wells of a multi-reaction plate to an analyzer using a large number of capillaries, such as an electrophoretic analyzer.

The present invention further relates to a method for transferring DNA sequencing samples utilizing the plate mentioned above, a method for purifying DNA sequencing samples utilizing said plate, and a method for purifying and transferring DNA sequencing samples utilizing said plate.

With recent developments of DNA detection methods utilizing laser fluorescence, laser fluorescence DNA sequencers have become widely used. Developments of such techniques have also enabled analysis of a large number of samples in, for example, genome researches and DNA diagnoses (approximately 100 lanes or less/2 operations/day/apparatus). Typical examples of such laser sequencers are those utilizing slab-type gels and capillary-type gels.

In order to analyze a larger number of samples than is possible by current techniques, equipment having a larger number of electrophoresis lanes (for example, 200 to 1000 lanes/operation) are required. Such equipment (including, for example multi-capillary sequencers) are under development.

However, as the number of lanes increases, the operation of transferring samples to the lanes becomes more time-consuming and more burdensome. That is, when a large number of samples are loaded on each of capillary gels, each sample should be injected into each capillary by contacting one end of the capillaries with a fine electrode lead. Therefore, development of a technique enabling quick and easy transfer of a large number of samples is urgently needed.

Further, introducing reaction solutions into the wells of micro-titer plates also requires more time as the number of the wells increases. Therefore, a means for rapidly introducing reaction solutions into the wells is also urgently desired.

Furthermore, following DNA sequencing reactions fragments of various lengths labeled with fluorescent labels are usually present with unreacted labeling reagent. The major part of such coexisting unreacted labeling reagent is usually not utilized in the reaction and exists in the reaction mixture in free form. If such a reaction solution is used for electrophoresis as it is, the high concentration of fluorescent label will migrate with the sample and can generate a signal markedly stronger than those produced by the target sequences. As a result, the desired analysis becomes impossible to perform. Accordingly, the fluorescent label should be removed before electrophoretic separation. However, removal of the unreacted labeling reagent in hundreds of samples requires much labor and time. As a result, even if efficiency of DNA sequencing methods itself is improved, the rate-determining factor would occur before sequencing.

SUMMARY OF THE INVENTION

Therefore, an object of the present invention is to provide a means of easily and rapidly introducing reactants into a large number of wells.

A further object of the present invention is to provide a method for easily and rapidly removing unreacted labeling substances and the like from a plurality of DNA sequencing samples containing the labeling substances.

A still further object of the present invention is to provide a means of easily and rapidly transferring a large number of DNA sequencing samples to electrophoretic capillaries.

Another object of the present invention is to provide a combined method for easily and rapidly removing unreacted labeling substances and the like from a plurality of DNA sequencing samples containing the labeling substances, and for easily and rapidly transferring a large number of DNA sequencing samples to electrophoretic capillaries in a short time.

PREFERRED EMBODIMENTS OF THE INVENTION

SUMMARY OF THE INVENTION

The first embodiment of the present invention relates to a part for assembling reaction vessels comprising a base plate with holes passing through said plate in the direction of thickness.

The second embodiment of the present invention relates to a method for preparation of reaction vessels containing a reaction solution comprising immersing the above-described plate according to the present invention in a reaction solution to introduce the reaction solution into the holes, and then sealing one of apertures of each hole with a membrane to complete said reaction vessels.

The third embodiment of the present invention relates to a plate used for transferring DNA sequencing samples to a separation/detection system comprising a base plate with holes passing through said plate in the direction of thickness and a membrane for sealing one of the apertures of each hole.

The fourth embodiment of the present invention relates to a method for removal of unreacted low molecular compounds contained in DNA sequencing samples comprising introducing said DNA sequencing samples into the holes of the plate according to the third embodiment of the present invention, providing a pressure difference between the remaining apertures of the holes and the outside of the sealing membrane in such a manner that the membrane side should have negative pressure to transfer said unreacted low molecular compounds in the DNA sequencing samples to the outside of the samples through said membrane.

The fifth embodiment of the present invention relates to a method for removal of unreacted low molecular compounds contained in DNA sequencing samples comprising introducing said DNA sequencing samples into the holes in the plate according to the third embodiment of the present invention, and applying a potential between said DNA sequencing samples and the outside of the sealing membrane such that said unreacted low molecular compounds in the DNA sequencing samples are transferred to the outside of the samples through said membrane.

The sixth embodiment of the present invention relates to a method for transferring DNA sequencing samples contained in the holes of the plate according to the third embodiment of the present invention to the capillaries of an electrophoretic separation/detection system wherein one of terminals of each capillary of the electrophoretic capillaries are inserted into said DNA sequencing samples and a potential is applied between said electrophoretic capillaries and the outside of the sealing membrane to transfer said DNA sequencing samples into the electrophoretic capillaries.

The seventh embodiment of the present invention relates to a method for transferring DNA sequencing samples to a separation/detection system comprising characterized in that said DNA sequencing samples are introduced into the holes of the plate according to the third embodiment of the present invention, one of terminals of each capillary of the electrophoretic capillaries is inserted into said DNA sequencing samples contained in the holes from the unsealed apertures and the contents are aspirated into the electrophoretic capillaries from the other terminal of each capillary of the electrophoretic capillaries to transfer target substances contained in said DNA sequencing samples into the electrophoretic capillaries.

The eighth embodiment of the present invention relates to a method for purification and transfer to a separation/detection system of DNA sequencing samples, which comprises removing unreacted low molecular compounds contained in the DNA sequencing samples and then transferring target substances contained in the DNA sequencing samples to electrophoretic capillaries for the separation/detection system, wherein said DNA sequencing samples are introduced into the holes of the plate according to the third embodiment of the present invention, one of terminals of each capillary of electrophoretic capillaries are inserted into said DNA sequencing samples, a potential is applied between the outside of said membrane sealing the holes containing said DNA sequencing samples and the other terminal of each capillary of the electrophoretic capillaries to transfer unreacted low molecular compounds contained in said DNA sequencing samples to the outside of the samples through the membrane, and then a potential is applied between the outside of said membrane and the other terminal of each capillary of the electrophoretic capillaries to transfer said target substances in the DNA sequencing samples into the electrophoretic capillaries.

The ninth embodiment of the present invention relates to a method for purification and transfer to a separation/detection system of DNA sequencing samples, which comprises removing unreacted low molecular compounds contained in the DNA sequencing samples and then transferring target substances contained in the DNA sequencing samples to electrophoretic capillaries for the separation/detection system, wherein said DNA sequencing samples are introduced into the holes of the plate according to the third embodiment of the present invention, a pressure difference is provided between the remaining apertures of the holes and the outside of the sealing membrane in such a manner that the membrane side has negative pressure to transfer said unreacted low molecular compounds in the DNA sequencing samples to the outside of the samples through said membrane, then one of terminals of each capillary of electrophoretic capillaries are inserted into said DNA sequencing samples, and a potential is applied between the outside of said membrane sealing the holes containing said DNA sequencing samples and the other terminal of each capillary of the electrophoretic capillaries to transfer said target substances contained in said DNA sequencing samples into the electrophoretic capillaries.

Part for assembling reaction vessels and method for preparing the same (the first and the second embodiments).

The part for assembling reaction vessels of the present invention consists of a base plate with holes passing through the plate in the direction of thickness. The part can be used for the preparation of reaction vessels containing a reaction solution. It will be explained hereinafter by the reference to FIG. 1.

Figure 1:
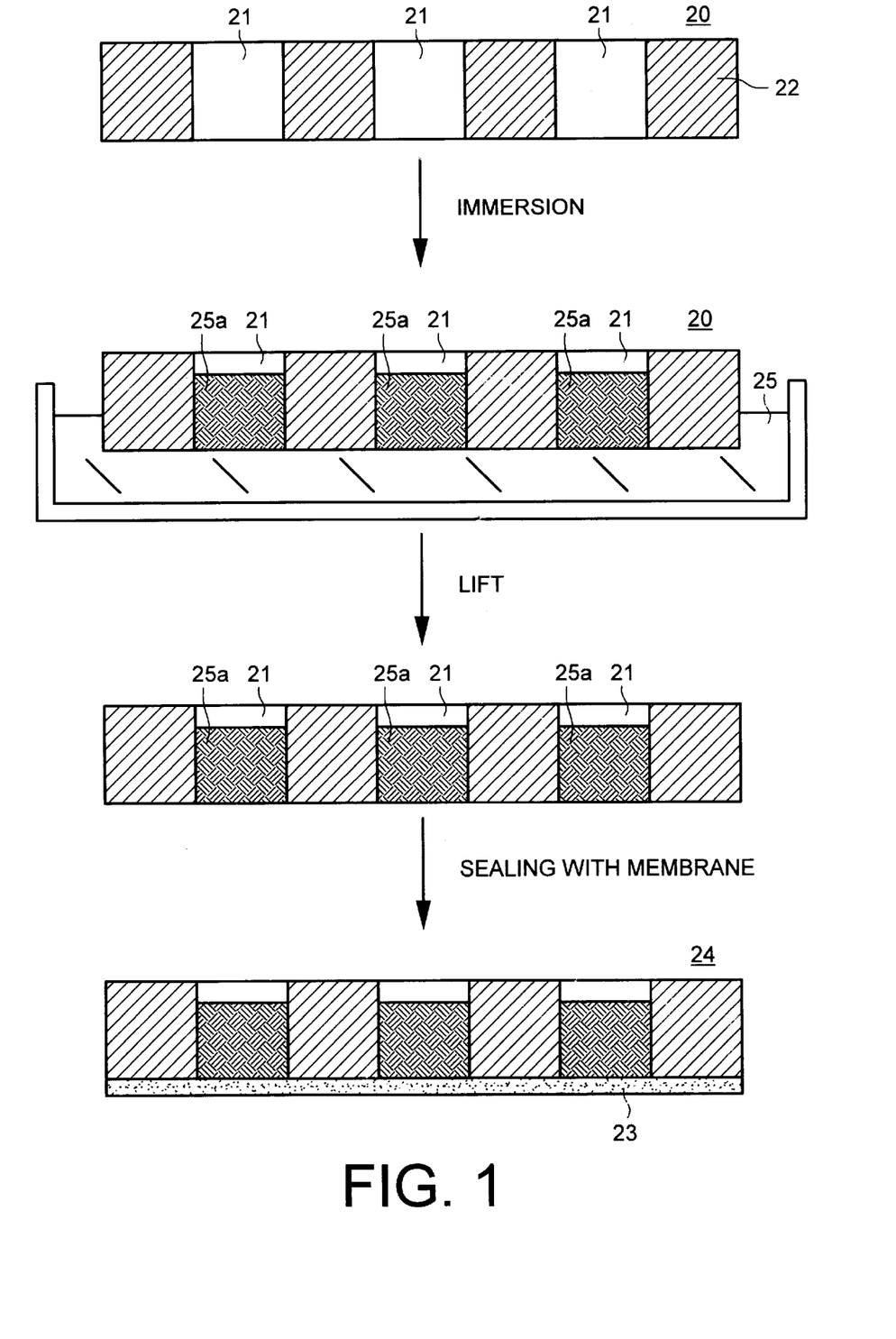
FIG. 1 is a schematic cross-sectional view illustrating a part for assembling reaction vessels of the present invention and the method for preparation of the vessels of the present invention containing a reaction mixture.

The part for assembling reaction vessels 20 consist of a base plate 22 with holes 21 passing through the plate in the direction of thickness. The base plate 22 can be made of, for example, synthetic resins, glass or the like. The size and the thickness of the plate can be suitably selected considering the size (inner diameter and depth) and the number of the holes 21. The size (inner diameter and depth) and the number of the holes 21 can be defined properly depending on the use of the plate. The inner diameter of the holes 21 may be, for example, 0.05 to 10 mm, preferably 0.5 to 5 mm. The depth of the holes 21 may be, for example, 0.2 to 200 mm. The number of the holes 21 is properly selected considering the number of electrophoretic capillaries, the performance of the separation/detection apparatus to be used, and the like. The larger the number of holes, the more samples can be processed simultaneously.

Vessels containing a reaction solution can be prepared by immersing the above-mentioned part for assembling reaction vessels 20 in a reaction solution 25 to introduce the solution 25a into the holes 21, and then sealing one of the apertures of each hole with a membrane 23 to obtain the reaction vessel 24.

The nature of the reaction solution is not particularly limited and it can be selected depending on the particular purpose. For example, the reaction solution can be a buffer solution containing various kinds of enzymes.

Plate for transfer to a separation/detection system (the third embodiment)

Figure 2:
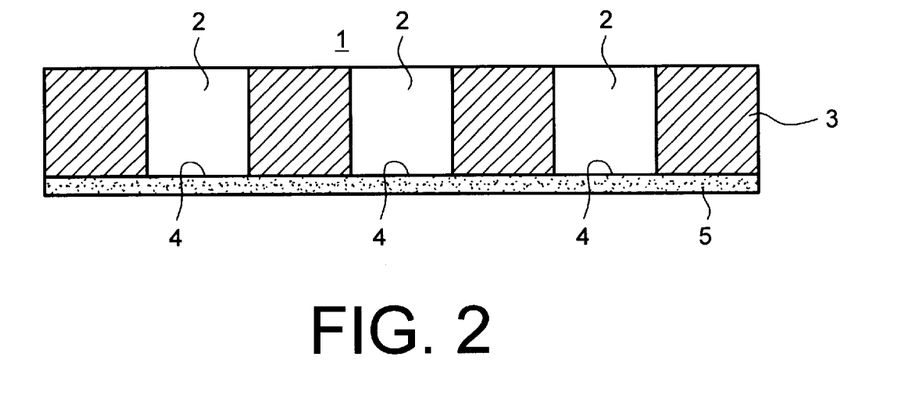
FIG. 2 is a schematic cross-sectional view of a plate according to the present invention for transferring DNA sequencing samples to a separation/detection system.

The plate for transfer to a separation/detection system of the present invention will be explained by the reference to FIG. 2.

A plate for transfer to a separation/detection system 1 consists of a base plate 3 with holes 2 passing through the plate in the direction of thickness and a membrane 5 provided for sealing one of apertures 4 of each hole 2.

The plate 3 can be made of, for example, synthetic resins, glass or the like and the size and the thickness thereof can be suitably selected considering the size (inner diameter and depth) and the number of the holes 2.

The size (inner diameter and depth) and the number of the holes 2 can also be suitably selected considering the use of the plate. The inner diameter of the holes 2 may be, for example, 0.1 to 5 mm, and the depth of the holes may be for example 0.2 to 200 mm. The number of the holes 2 is properly selected depending on the number of electrophoretic capillaries, the performance of the separation/detection system to be used, and the like. The larger the number of holes, the more samples can be processed simultaneously.

Material of the membrane 5 can be suitably selected depending on the use of the plate. For example, when target substances in DNA sequencing samples are electrically transferred to the electrophoretic capillaries, the membrane 5 can be made of a material capable of conducting electricity when contacting with an electrolyte. For example, it can be a membrane used as a separator membrane for molecular sieving such as ultrafiltration membranes.

When target substances in DNA sequencing samples are transferred to the electrophoretic capillaries by utilizing a pressure difference, the membrane 5 may be a liquid permeating material, such as a membrane of cellophane, polyether sulfone or the like.

When unreacted low molecular compounds in the DNA sequencing sample are electrically removed from the system through the membrane 5, the membrane 5 can be a material which permeates the low molecular compounds but not reaction products, i.e., DNA fragments. For example, an ultrafiltration membrane can be used.

Further, when the unreacted low molecular compounds in the DNA sequencing samples are removed electrically from the system through the membrane 5 and then the target substances in the DNA sequencing samples are electrically transferred to the electrophoretic capillaries, the membrane 5 can be a material which is permeable to low molecular weight compounds but not to the reaction products, i.e., DNA fragments, and which is capable of conducting electricity when contacting with an electrolyte. As such a membrane, for example, an ultrafiltration membrane can be employed.

As the ultrafiltration membrane of the plate of the present invention, a polyether sulfone membrane can be used.

Method for removing unreacted low molecular compounds (Pressure difference method) (the fourth embodiment)

Figure 3:
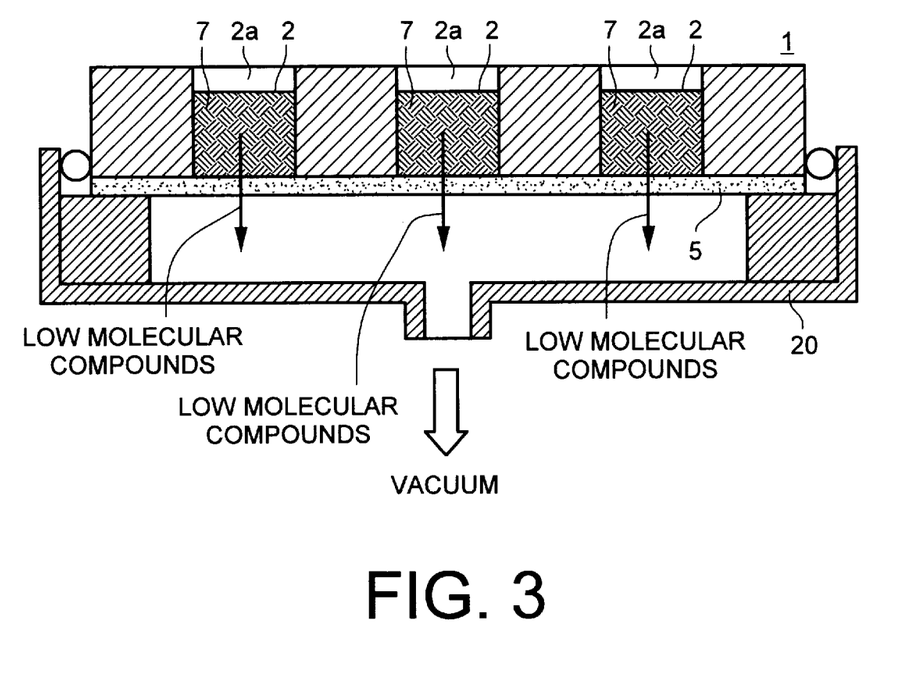
FIG. 3 is a schematic cross-sectional view illustrating a method according to the present invention for removal of unreacted low molecular compounds (pressure difference method).

The method will be explained hereinafter by reference to FIG. 3.

As the DNA sequencing samples 7 are introduced into the holes 2 of the plate 1 of the present invention a pressure difference is provided between the apertures 2a of the holes and the outside of the membrane 5 so that the outside of the membrane 5 should have negative pressure. More specifically, the pressure difference can be produced so that the outside of the membrane 5 should have negative pressure by providing a vacuum container 20 on the plate 1 at the membrane side and reducing the pressure therein. The unreacted low molecular weight compounds in the DNA sequencing samples can be transferred to the outside of the samples through the membrane 5 together with the other low molecular weight compounds such as water.

Method for removing unreacted low molecular weight compounds (electrical method) (the fifth embodiment)

The fifth embodiment may be exemplified by the following two methods.

Figure 5:
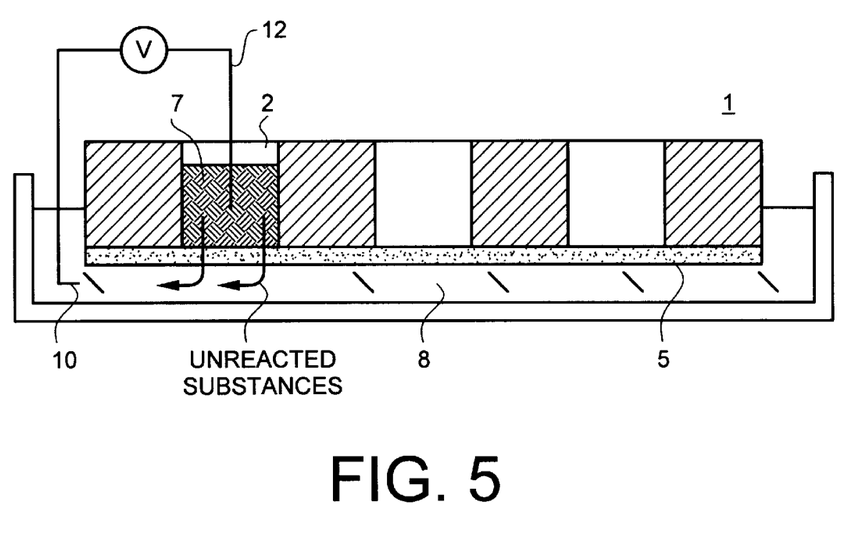
FIG. 5 is a schematic cross-sectional view illustrating a method according to the present invention for removal of unreacted low molecular compounds (electrical method).

In the first method, terminals of electrophoretic capillaries are inserted into the DNA sequencing samples respectively, wherein the other terminals of said capillaries are contacted with an electrolyte having an electrode (1); the sealing membranes are contacted with an electrolyte with which an electrode (2) is contacted; and a potential is applied between the electrodes (1) and (2). This method in which an electrode is immersed in the DNA sequencing sample is shown in FIG. 5.

As an electrode 12 is immersed into the DNA sequencing sample 7 contained in the hole 2 of the plate 1, a potential is applied between the outside of the membrane 5 and the electrode 12 so that the electrode 12 is a cathode. In this manner, the unreacted low molecular compounds in the DNA sequencing sample 7 can be transferred to the outside of the sample 7 through the membrane 5 as well. Although FIG. 5 shows the above-described operation for only one of the through-holes 2, the operation of transferring the low molecular compounds can be carried out for a plurality of or all of the holes 2 simultaneously.

In the this method, unreacted low molecular weight compounds in the DNA sequencing samples within a plurality of or all of the holes are simultaneously transferred through the membrane 5 to the outside of the samples by contacting the whole surface of the membrane 5 of the plate 1 with the electrolyte 8, immersing each electrode 12 or each capillary 6 of electrophoretic capillaries in the sample in each of the holes and applying a potential thereto.

In the second method, electrodes are inserted into the DNA sequencing samples; the sealing membrane are contacted with an electrolyte with which an electrode is contacted; and a potential is applied between the electrodes inserted in the DNA sequencing samples and the electrode contacted with the electrolyte. This method will be explained by reference to FIG. 4.

Figure 4:
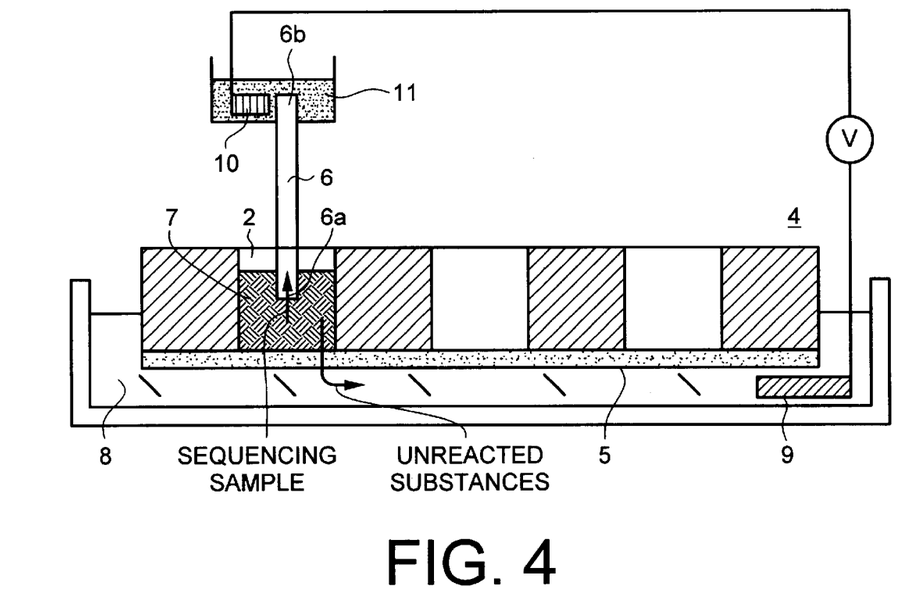
FIG. 4 is a schematic cross-sectional view illustrating a method according to the present invention for removal of unreacted low molecular compounds (electrical method) and a method according to the present invention for transferring DNA sequencing samples to a separation/detection system (electrical method).

As one of the terminals 6a of each electrophoretic capillary 6 is immersed into the DNA sequencing sample 7 contained in each hole 2 of the plate 1, a potential is applied between the outside of the membrane 5 and the other terminal 6b of the capillary 6 so that the other terminal 6b of the capillary 6 should be a cathode. The potential can be applied by using an electrode 9 as an anode and an electrode 10 as a cathode and contacting the membrane 5 with an electrolyte 8 where the electrode 9 is immersed and the other terminal 6b of the electrophoretic capillary 6 with an electrolyte 11 where the electrode 10 is immersed.

In this manner, the unreacted low molecular compounds within the DNA sequencing sample 7 can be transferred to the outside of the sample through the membrane 5. Although FIG. 4 shows the above-described operation for only one of the holes 2, the operation of transferring the low molecular weight compounds can be carried out for a plurality of or all of the holes 2 simultaneously.

Method for transfer to separation/detection system (electrical method) (the sixth embodiment)

This method is for transferring the DNA sequencing samples contained in the holes of the plate of the present invention to each of the electrophoretic capillaries for separation and detection. It will be explained by reference to FIG. 4.

As one of terminals 6a of each capillary 6 of the electrophoretic capillaries is immersed into the DNA sequencing sample 7 contained in the hole 2, a potential is applied between the outside of the membrane 5 and the other terminal 6b of the capillary 6. The potential can be applied, as shown in FIG. 4, between the electrode 9 used as a cathode and the electrode 10 used as an anode, while the membrane 5 is in contact with an electrolyte 8 wherein the electrode 9 is immersed and the other terminal 6b of the capillary 6 is in contact with an electrolyte 11 wherein the electrode 10 is immersed.

This electrical injection method can be used whether the electrophoretic capillaries (separation system) contain a polymer solution or an acrylamide gel. An electric voltage of 1 to 10 kV is applied between the electrode 9 and the electrode 10 for one to several tens of seconds to carry out the injection electrophoretically.

Thus, the target substances in the DNA sequencing sample 7 can be transferred to each of the electrophoretic capillaries 6 (around the terminal 6a).

Although FIG. 4 shows the above-mentioned operation for only one of the holes 2, the target substances in the DNA sequencing samples within a plurality of or all of the holes are transferred into the capillaries simultaneously, by contacting the whole surface of the membrane 5 of the plate 1 with an electrolyte 8 and placing the other terminal 6b of each electrophoretic capillary 6 on the anode side.

Method for transfer to separation/detection system (Pressure difference method (the seventh embodiment)

Figure 6:
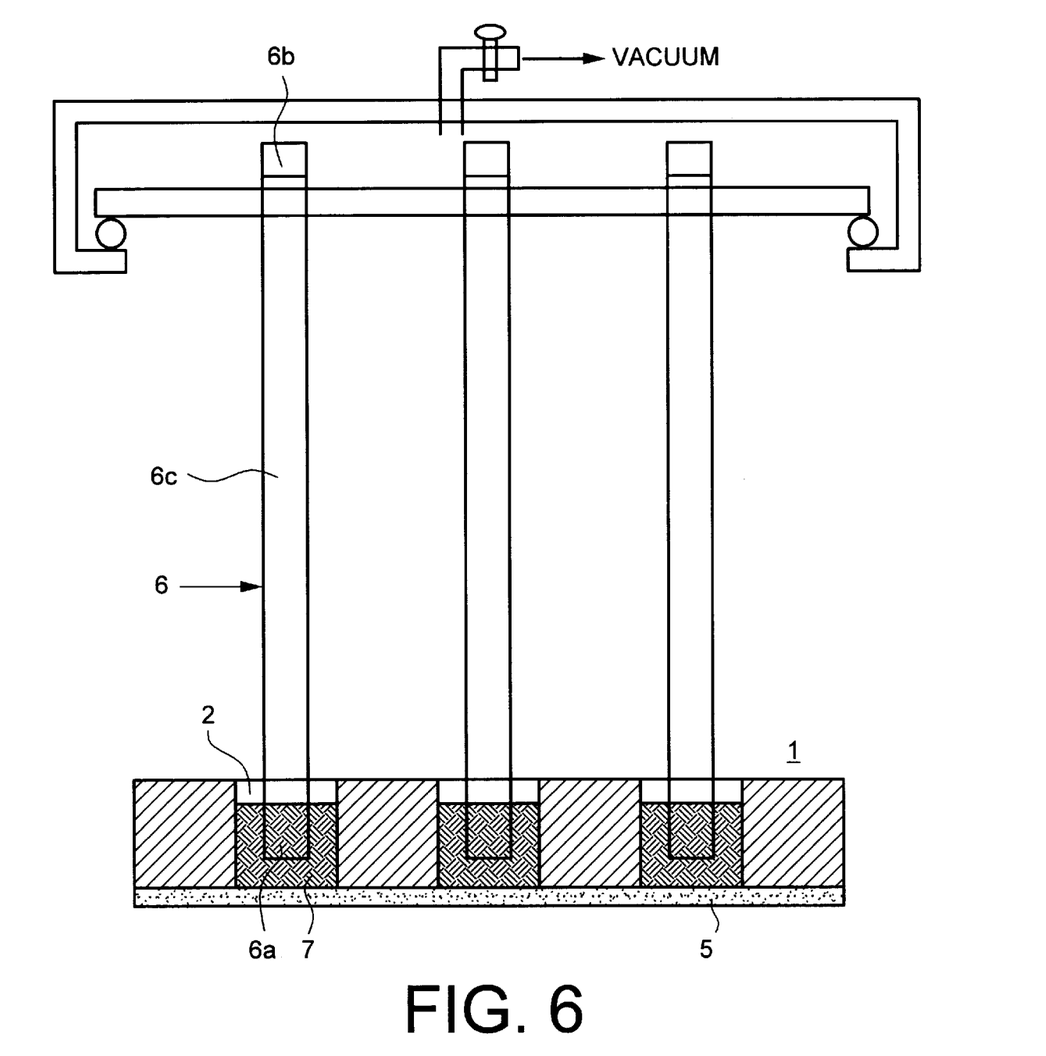
FIG. 6 is a schematic cross-sectional view illustrating a method according to the present invention for transferring DNA sequencing samples to a separation/detection system (pressure difference method).

This method is for transferring the DNA sequencing samples contained within the holes of the plate of the present invention to each of the electrophoretic capillaries for separation and detection, and it will be explained by reference to FIG. 6.

As the DNA sequencing sample 7 is introduced into the holes 2 of the plate 1, one of terminals 6a of each capillary of electrophoretic capillaries 6 is immersed in the DNA sequencing sample 7 in the hole 2 from the aperture of the hole 2. Then, the contents 6c (for example, a polymer solution) of the electrophoretic capillary 6 are aspirated from the other terminal 6b of the electrophoretic capillary 6. Thus, the target substances contained in the DNA sequencing sample 7 can be transferred into the electrophoretic capillary 6.

The target substances contained in the DNA sequencing samples 7 of every hole 2 can be transferred to each of electrophoretic capillaries simultaneously by immersing each of electrophoretic capillaries 6 into each of the holes 2 of the plate 1 respectively and aspirating them simultaneously.

Method for transfer to purification/separation/detection system (the eighth embodiment)

This method is for removing unreacted low molecular weight compounds in the DNA sequencing samples and then transferring the target substances in the DNA sequencing samples to electrophoretic capillaries for separation and detection. In this method, the above-mentioned method for removing unreacted low molecular weight compounds contained in the DNA sequencing samples and the above method for transferring the DNA sequencing samples to separation/detection system are carried out successively.

The method of the fifth embodiment of the present invention is used for removing low molecular weight compounds. Specifically, as shown in FIG. 4, as one of the terminals 6a of each electrophoretic capillary 6 is immersed into the DNA sequencing sample 7 contained in the hole 2 of the plate 1 of the present invention, a potential is applied between the outside of the membrane 5 and the other terminal 6b of the capillary 6 so that the other terminal 6b should be a cathode to transfer the unreacted low molecular compounds in the DNA sequencing sample 7 to the outside of the sample through the membrane 5.

Then, the method of the sixth embodiment of the present invention is employed for transfer of the sample. Specifically, the target substances in the DNA sequencing sample 7 are transferred to the electrophoretic capillary 6 by applying a potential between the outside of the membrane 5 and the other terminal 6b of each electrophoretic capillary 6 so that the other terminal 6b should be an anode.

Removal of the low molecular weight compounds and transfer of the target substances can readily be conducted by reversing the polarity of the electrodes 9 and 10. However, the electrolyte 8 containing the unreacted low molecular weight compounds transferred through the membrane 5 is preferably changed before the transfer of the target substances in order to prevent the low molecular weight compounds from returning into the sample 7.

Method for transfer to purification/separation/detection system (the ninth embodiment)

This method is for removing the unreacted low molecular weight compounds in the DNA sequencing samples and transferring the target substances in the DNA sequencing samples to electrophoretic capillaries for separation and detection. In this method, the above-mentioned method for removing unreacted low molecular weight compounds in the DNA sequencing samples and the above method for transferring the DNA sequencing samples to a separation/detection system are carried out successively.

The method of the fourth embodiment of the present invention is employed for removing low molecular compounds. Specifically, as shown in FIG. 3, as the DNA sequencing sample 7 is introduced into the holes 2 of the plate 1 of the present invention, a pressure difference is provided between the apertures 2a of the holes and the outside of the membrane 5 so that the outside of the membrane 5 should have negative pressure. More specifically, the pressure difference can be provided so that the outside of the membrane 5 should have negative pressure by providing a vacuum container 20 on the plate 1 at the membrane 5 side and reducing the pressure therein. The unreacted low molecular weight compounds in the DNA sequencing sample can be transferred to the outside of the sample through the membrane 5 together with the other low molecular weight compounds such as water.

Then, the method of the sixth embodiment of the present invention is used for transfer of the sample. Specifically, as shown in FIG. 4, as one of the terminals 6a of each electrophoretic capillary 6 is immersed into the DNA sequencing sample 7 contained in the hole 2 of the plate 1 of the present invention, a potential is applied between the outside of the membrane 5 and the other terminal 6b of the capillary 6 to transfer the target substances in the DNA sequencing sample 7 to the inside of the electrophoretic capillaries 6.

The DNA sequencing samples used in the present invention may be, for example, products of a large number of chemical reactions or enzymatic reactions (96 or more reactions/plate/operation) produced in a large number of spaces (wells, holes etc.). Nature, number and the like of the reactions are not particularly limited. For example, the DNA sequencing samples may be products of DNA sequencing reactions carried out in the holes of the plate of the present invention or products of DNA sequencing reactions carried out in wells of a conventional micro-titer plate. Further, DNA sequencing reactions suitable for use in the present invention include Sanger reactions using dideoxynucleotides, DNA cycle sequencing conducted by using PCR (polymerase chain reaction), and the like.

When DNA sequencing reactions are carried out in the spaces formed by the holes of the plate of the present invention, the following procedure is preferably employed. First, reagents and enzymes, other than those required to be of different kind for each hole (for example, template DNA and the like), such as reaction enzyme (thermostable polymerase or the like), reaction buffer and the like are introduced together into each hole of the part for assembling reaction vessels of the first embodiment of the present invention as explained in the second embodiment of the present invention. That is, a certain pre-determined amount of a reagent and/or enzyme solution can be introduced into each of the holes simply by immersing the part for assembling reaction vessels according to the first embodiment of the present invention into the reagent and/or enzyme solution and pulling the part up from the solution. When the plate is provided with two or more kinds of holes with different sizes, reaction vessels capable of inclusion of different amounts of reagent and/or enzyme solution can be formed. Then, a membrane is applied to one surface of the plate of the part to complete a plate retaining the reagent and/or enzyme solution in its holes.

The obtained plate can be used for desired reactions such as DNA sequencing reactions or the like.

As the reactions carried out in the vessels, sequencing reactions performed at 37° C. and utilizing DNA polymerase are advantageous because of the reaction solution-retaining property of the membrane. This technique of the present invention dramatically simplifies the procedure of simultaneously introducing the reagent and/or enzyme solution into multiple reaction spaces. However, instead of using this technique, the reagent and/or enzyme solution may be introduced into the reaction spaces one by one.

Figure 7:
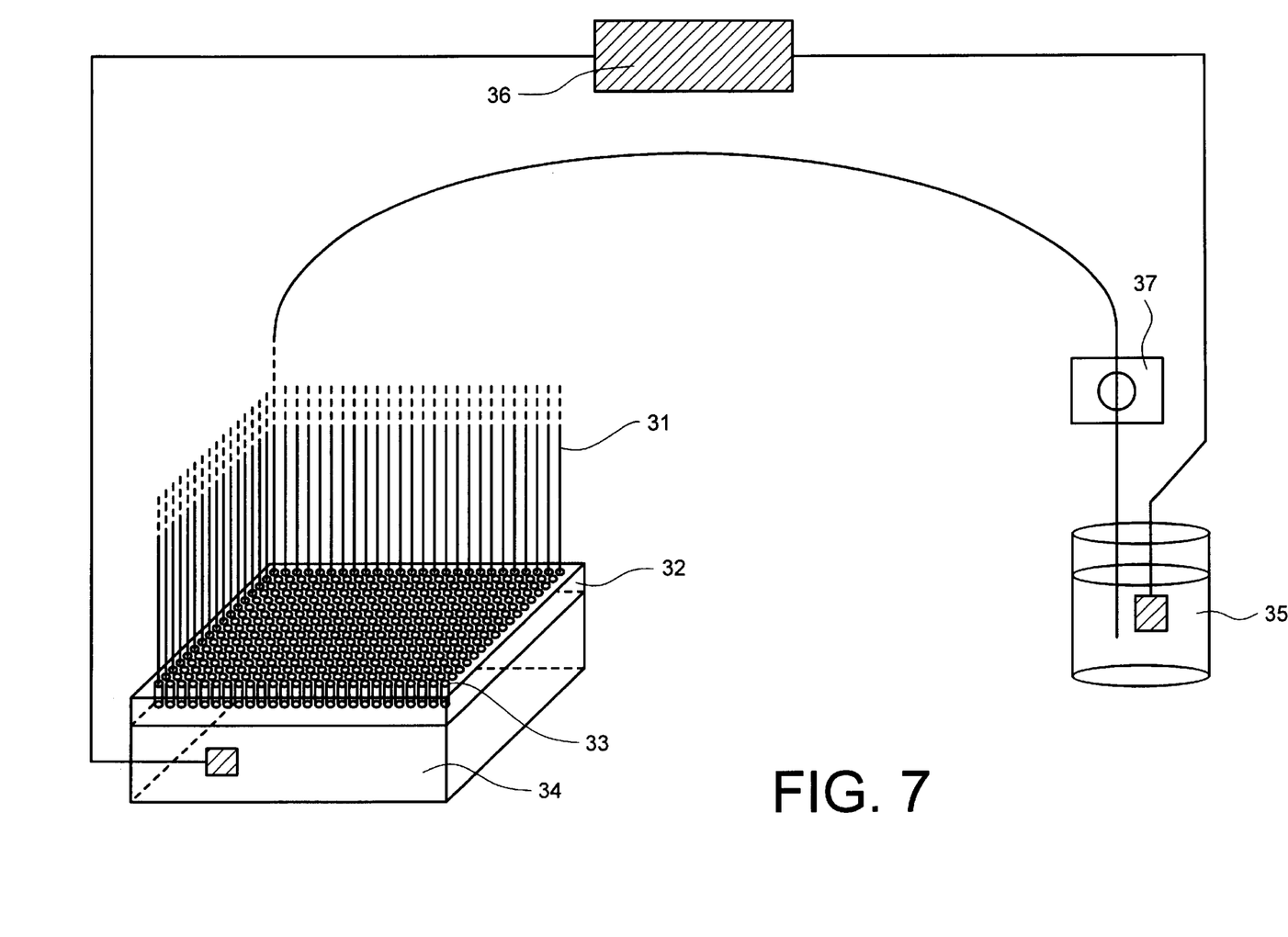
FIG. 7 is a schematic view illustrating a method for separation and detection by electrophoresis.

The target substances transferred to electrophoretic capillaries by the method of the present invention can be separated and detected by conventional methods, such as the DNA sequencing technique based on DNA capillary electrophoresis. As a DNA separation system used for DNA capillary electrophoresis, for example, as shown in FIG. 7 capillary lanes 31 may be provided in a three-dimensionally regular grid-like arrangement (for example, like parallel columns). The grid-like arrangement of the capillaries can correspond to the arrangement of the holes 33 of the multi-hole plate 32 of the present invention so that each capillary should be inserted into each corresponding hole 33 of the multi-hole plate 32.

The membrane (not shown) provided on the bottom surface of the multi-hole plate 32 provided with the capillaries is contacted with the upper surface of buffer contained in a cathode electrophoretic bath 34. A potential is applied by means of an electric source 36 between the cathode electrophoretic bath 34 and an anode electrophoretic bath 35 in which the other terminal of each capillary is immersed. Thus, all of the target substances in the multi-hole plate 32 are electrophoretically injected into the capillaries. Then, the target substances are separated electrophoretically and separated fragments are detected by a detector 37. The detector 37 is selected depending on the nature of the marker on the fragments. For example, when the marker is a fluorescence marker, a fluorescence detector is used, and an imaging analyzer can be used for an RI marker.

EXAMPLES

The present invention will be further illustrated by the reference to the following examples.

Figure 8:
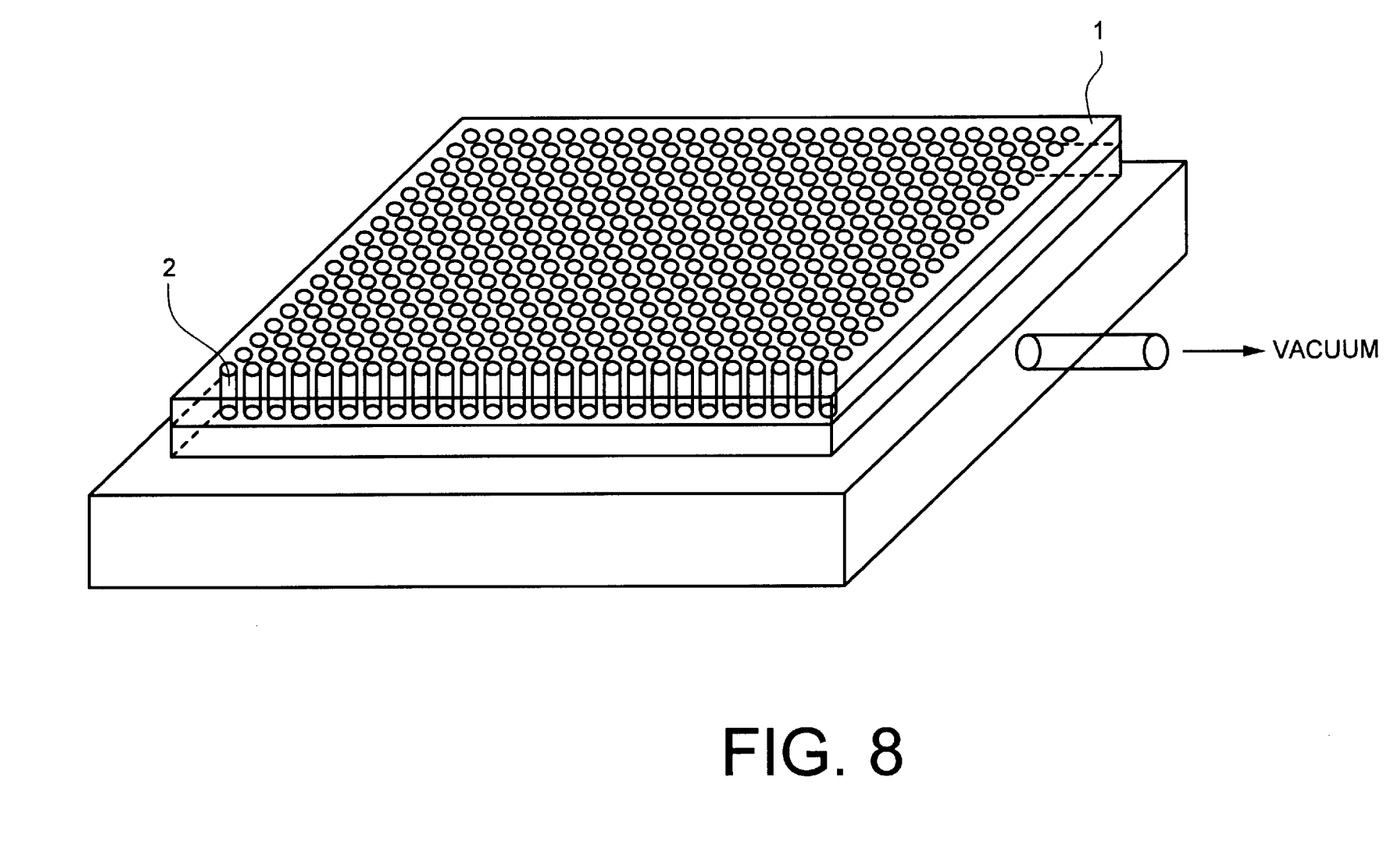
FIG. 8 is a schematic view illustrating a method for removal of unreacted low molecular compounds (pressure differentiation method).
Figure 9:
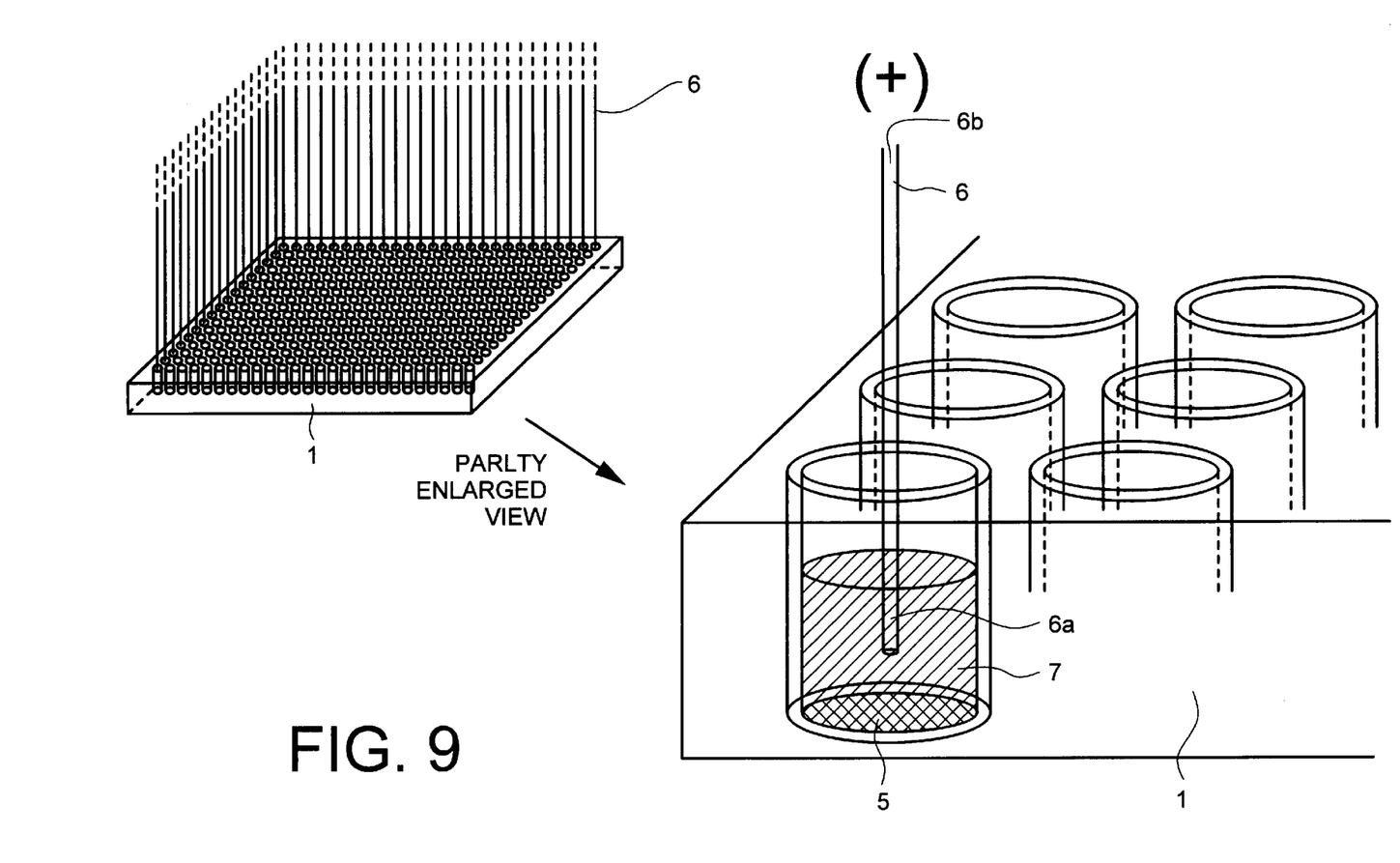
FIG. 9 is a schematic view illustrating a method for transferring DNA sequencing samples to electrophoretic capillaries (electrical method).

In the following examples, unreacted low molecular weight compounds contained in DNA sequencing samples were removed by using an apparatus as shown in FIG. 8, and then DNA sequencing samples were transferred to electrophoretic capillaries by using a capillary electrophoresis apparatus as shown in FIG. 9. Further, separation and detection were performed by a separation/detection apparatus utilizing electrophoresis as shown in FIG. 7.

(1) Pretreatment of inner walls of quartz capillary A quartz capillary having an inner diameter of 0.1 mm and an outer diameter of 0.22 mm (O.D. 220 $\mu$m, I.D. 100 $\mu$m, SGE: Australia) was cut into capillaries having a length of 30 cm, immersed into a solution of functional regents (3-methacryloxypropyltrimethoxysilane etc.) and left for several hours. Then, the inside of the capillaries was washed with water and methanol.

(2) Introduction of acrylamide

An acrylamide solution [TBE buffer (100 mM Tris borate, pH 8.0, 0.2 mM EDTA), 7M urea, 6% acrylamide, 0 to 5% bisacrylamide] was prepared, degassed by a vacuum machine or the like, added with ammonium persulfate (final concentration: 0.05%) and tetramethylethylenediamine (final concentration: 0.01%), and introduced into the above quartz capillaries using an injection syringe. The capillaries were left for several hours at 4° C. for completion of gelation.

(3) Preparation of template DNA

M18 primer (0.5 pmol), template DNA (M13 phage, 0.5 pmol), Sequenase Ver. 2.0 buffer (2 $\mu$l, 200 $\mu$M Tris-Cl, pH 7.5, 100 mM MgCl$_2$, 250 mM NaCl) were introduced into a sampling tube and adjusted to 10 $\mu$l with sterile distilled water to obtain a mixture. The mixture was warmed at 65° C. for 10 minutes and returned to room temperature to cause annealing of the template and the primer. Then, the solution of the annealed template/DNA-primer (10 $\mu$l) was added with 0.1M dithiothreitol (1 $\mu$l), dNTPs mix (2 $\mu$l, 1 $\mu$M dATP, dGTP, dTTP), [$\alpha$-$^{32}$P] dCTP (0.5 $\mu$l, 300 Ci/mmol, 10 mCi/ml, Amersham) and Sequenase Ver. 2.0 (2U, Amersham). Then the reaction mixture (2.5 $\mu$l) was added to a termination mixture (3.5 $\mu$l, 80 $\mu$M dATP, dGTP, dCTP, dTTP, 8 $\mu$M ddTTP, 50 mM NaCl), mixed and allowed to react at 37° C. for 10 minutes. The reaction mixture was mixed with 10 $\mu$l of formamide dye [95% formamide, 10 mM EDTA, 0.05% Bromophenol Blue (BPB), 0.05% xylene cyanol (KC)] and heated to 80° C. for 5 minutes.

(4) Injection of samples and electrophoresis

A polyether sulfone ultrafiltration membrane was fused by an adhesion method such as ultrasonic bonding to a bottom surface (to be contacted with buffer) of a plate having 384 (16×24) through-holes having an inner diameter of 3.5 mm. The sample solution prepared as above was injected to each through-hole of the plate so that the sample solution should contact with the ultrafiltration membrane.

The plate 1 with the membrane containing the sample solution was connected with an aspirator as shown in FIG. 8 and aspirated by vacuuming from the membrane side for 10 minutes to reduce the pressure so that unreacted low molecular weight compounds were removed.

Then, each one terminals 6b of the above-prepared capillaries 6 containing acrylamide gel was immersed into a TBE buffer (not shown) and the other terminal was immersed into the sample solution 7 as shown in FIG. 9. The ultrafiltration membrane 5 provided on the bottom surface of the plate 1 was immersed into a TBE buffer. A voltage of 3 kV was applied between the cathode electrophoretic bath 34 and the anode electrophoretic bath 35 for 30 seconds as shown in FIG. 7.

Then, the terminals of the capillaries immersed in the samples were transferred to a TBE buffer and electrophoresis was performed at 3000 V for 1 hour.

(5) Autoradiography

Figure 10:
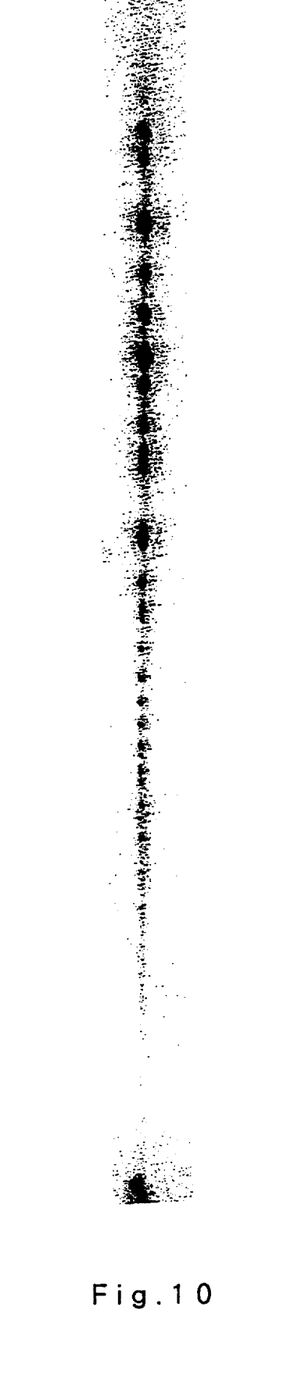
FIG. 10 shows a sequencing ladder of a migration pattern obtained by an imaging analyzer.

When BPB reached the bottom ends of the capillaries, electrophoresis was finished, and the migration pattern was analyzed by BAS 2000 imaging analyzer (FUJI) . The result is shown in FIG. 10. A sequencing ladder was obtained by the above protocol as shown in FIG. 10.

According to the present invention, a means of easily introducing reaction solutions into a large number of wells in a short time is provided.

According to the present invention, a method for easily removing unreacted labeling substances and the like in a short time from a plurality of DNA sequencing samples containing the labeling substances and the like is also provided.

According to the present invention, a means of easily transferring a large number of DNA sequencing samples to electrophoresis capillaries in a short time is also provided.

In addition, according to the present invention, a method for easily removing unreacted labeling substances and the like in a short time from a plurality of DNA sequencing samples containing the labeling substances and the like and capable of easily transferring a large number of DNA sequencing samples to electrophoresis capillaries in a short time is also provided.

What I claim is:

1. A method for preparation of reaction vessels containing a reaction solution comprising immersing a part comprising
    a base plate with holes passing completely through said plate such that each hole has two apertures, one on each side of said base plate, and wherein
        each of said holes is suitable for containing reaction solutions when one of the apertures of said hole is sealed,
    in a reaction solution introduce the reaction solution into the holes, and then sealing one of the apertures of each hole with a membrane, thus forming reaction vessels containing said reaction solution.

2. The method of claim 1 wherein the reaction solution is a buffer solution containing an enzyme.

3. A method for removal of unreacted low molecular weight compounds contained in DNA sequencing samples comprising introducing said DNA sequencing samples into the holes of a plate, said plate comprising a base plate with holes passing completely through said plate such that each hole has two apertures, one on each side of said base plate, and an ultrafiltration membrane sealing one of the apertures of each hole wherein said membrane comprises an electrically conductive material or a liquid-permeable material, creating a pressure difference between the opening of each hole and the outside of the sealing membrane such that the pressure is relatively lower on the membrane side, thereby transferring said unreacted low molecular weight compounds from the DNA sequencing samples through said membrane.

4. The method of claim 3 wherein the unreacted low molecular weight compounds are unreacted fluorescence labeling compounds.

5. The method of claim 3 wherein said DNA sequencing samples are products of DNA sequencing reactions conducted in reaction solutions contained by the plate.

6. The method of claim 3 wherein said DNA sequencing samples are products of DNA sequencing reactions conducted in a micro-titer plate.

7. A method for removal of unreacted low molecular weight compounds contained in DNA sequencing samples, comprising introducing said DNA sequencing samples into the holes of a plate, said plate comprising a base plate with holes passing completely through said plate such that each hole has two apertures, one on each side of said base plate, and an ultrafiltration membrane sealing one of the apertures of each hole wherein said membrane comprises an electrically conductive material or a liquid-permeable material, and applying a potential between said DNA sequencing samples and the outside of the sealing membrane such that said unreacted low molecular weight compounds in the DNA sequencing samples are transferred through said membrane.

8. The method of claim 7, further comprising inserting one terminal of electrophoretic capillaries into the DNA sequencing samples, contacting the other terminal of said capillaries with an electrolyte contacting an electrode (1); contacting the sealing membrane with an electrolyte with which an electrode (2) is contacted; and applying a potential between the electrodes (1) and (2).

9. The method of claim 7, further comprising inserting electrodes into the DNA sequencing samples contacting an electrode with the electrolyte; and applying a potential between the electrodes inserted in the DNA sequencing samples and the electrode contacted with the electrolyte.

10. The method of claim 7 wherein the unreacted low molecular weight compounds are unreacted fluorescence labeling compounds.

11. The method of claim 7 wherein said DNA sequencing samples are products of DNA sequencing reactions conducted in reaction solutions contained by the plate.

12. The method of claim 7 wherein said DNA sequencing samples are products of DNA sequencing reactions conducted in the wells of a micro-titer plate.

13. A method for purification and transfer to a separation and/or detection system of DNA sequencing samples, which comprises removing unreacted low molecular weight compounds contained in the DNA sequencing samples and then transferring target substances contained in the DNA sequencing samples to electrophoretic capillaries for the separation and/or detection system, wherein said DNA sequencing samples are introduced into the holes of a plate, said plate comprising a base plate with holes passing completely through said plate such that each hole has two apertures, one on each side of said base plate, and an ultrafiltration membrane sealing one of the apertures of each hole wherein said membrane comprises an electrically conductive material or a liquid-permeable material, one terminal of an electrophoretic capillary is inserted into each of said DNA sequencing samples, a potential is applied between the outside of said membrane sealing the holes containing said DNA sequencing samples and the other terminal of each capillary of the electrophoretic capillaries such that unreacted low molecular weight compounds contained in said DNA sequencing samples are transferred through the membrane, and then a potential is applied between the outside of said membrane, and the other terminal of each electrophoretic capillary to transfer said target substances in the DNA sequencing samples into the electrophoretic capillaries.

14. A method for purification and transfer to a separation and/or detection system of DNA sequencing samples, which comprises removing unreacted low molecular weight compounds contained in the DNA sequencing samples and then transferring target substances contained in the DNA sequencing samples to electrophoretic capillaries for the separation and/or detection system, characterized in that said DNA sequencing samples are charged in the holes of a plate, said plate comprising a base plate with holes passing completely through said plate such that each hole has two apertures, one on each side of said base plate, and an ultrafiltration membrane sealing one of the apertures of each hole wherein said membrane comprises an electrically conductive material or a liquid-permeable material, a pressure difference is provided between the remaining apertures of the holes and the outside of the sealing membrane in such a manner that the membrane side should have negative pressure to transfer said unreacted low molecular weight compounds in the DNA sequencing samples to the outside of the samples through said membrane, then one of terminals of each capillary of electrophoretic capillaries are inserted into said DNA sequencing samples, and a potential is applied between the outside of said membrane sealing the holes charged with said DNA sequencing samples and the other terminal of each capillary of the electrophoretic capillaries to transfer target substances contained in said DNA sequencing samples to the electrophoretic capillaries.

* * * * *